(12) United States Patent
Bader et al.

(10) Patent No.: US 9,962,301 B2
(45) Date of Patent: May 8, 2018

(54) ABSORBENT ARTICLE WITH COMPOUND MATERIAL WEB

(71) Applicant: The Procter & Gamble Company, Cincinnati, OH (US)

(72) Inventors: Herbert Bader, Norwalde (DE); Marcel Groβmann, Essen (DE)

(73) Assignee: The Procter & Gamble Company, Cincinnati, OH (US)

( * ) Notice: Subject to any disclaimer, the term of this patent is extended or adjusted under 35 U.S.C. 154(b) by 783 days.

(21) Appl. No.: 14/546,291

(22) Filed: Nov. 18, 2014

(65) Prior Publication Data
US 2015/0173982 A1    Jun. 25, 2015

Related U.S. Application Data

(60) Provisional application No. 61/917,956, filed on Dec. 19, 2013.

(51) Int. Cl.
| | |
|---|---|
| A61F 13/62 | (2006.01) |
| A61F 13/49 | (2006.01) |
| A61F 13/56 | (2006.01) |
| A44B 18/00 | (2006.01) |

(52) U.S. Cl.
CPC ...... *A61F 13/625* (2013.01); *A61F 13/49015* (2013.01); *A61F 13/5622* (2013.01); *A44B 18/0015* (2013.01)

(58) Field of Classification Search
CPC ............... A44B 18/0015; A61F 13/625; A61F 13/49015
See application file for complete search history.

(56) References Cited

U.S. PATENT DOCUMENTS

| | | | | |
|---|---|---|---|---|
| 5,476,702 A * | 12/1995 | Datta | ............... | A61F 13/627 428/157 |
| 5,786,061 A * | 7/1998 | Banfield | ............ | A44B 18/0076 24/442 |
| 5,846,262 A | 12/1998 | Sayama et al. | | |
| 6,730,069 B2 * | 5/2004 | Tanzer | ............... | A61F 13/5622 24/442 |

(Continued)

FOREIGN PATENT DOCUMENTS

| | | |
|---|---|---|
| EP | 768075 B1 | 2/2003 |
| EP | 1736306 A1 | 12/2006 |

(Continued)

OTHER PUBLICATIONS

International Search Report, PCT/US2014/066638, dated Mar. 11, 2015, 10 pages.

*Primary Examiner* — Susan Su
(74) *Attorney, Agent, or Firm* — Wednesday G. Shipp (57) ABSTRACT

A closure element comprising a composite web comprising: a nonwoven web; an elastically extensible film strip joined to the top surface of the nonwoven web; a nonwoven material disposed on top of the film strip; and a strip of a fastening material disposed on top of the nonwoven web, wherein the nonwoven material overlaps the edges of the strip of fastening material and the strip of fastening material at its edges overlapped by the nonwoven material has projections which extend into the nonwoven material, as well as absorbent articles that include closure elements.

8 Claims, 10 Drawing Sheets

(56) References Cited

U.S. PATENT DOCUMENTS

| | | | |
|---|---|---|---|
| 7,032,278 B2 * | 4/2006 | Kurtz, Jr. | A44B 18/0003 |
| | | | 24/442 |
| 7,422,991 B2 | 9/2008 | Baldauf et al. | |
| 8,337,651 B2 | 12/2012 | Schoenbeck | |
| 8,496,773 B2 | 7/2013 | Bader et al. | |
| 9,480,612 B2 * | 11/2016 | Bader | A61F 13/625 |
| 9,849,043 B2 * | 12/2017 | Barnes | A61F 13/622 |
| 2004/0172792 A1 * | 9/2004 | Kurtz, Jr. | A44B 18/0003 |
| | | | 24/442 |
| 2005/0132543 A1 * | 6/2005 | Lindsay | A44B 18/0015 |
| | | | 24/442 |
| 2006/0287637 A1 | 12/2006 | Lam et al. | |
| 2006/0292328 A1 * | 12/2006 | Baldauf | A61F 13/4902 |
| | | | 428/77 |
| 2011/0092946 A1 | 4/2011 | Kline et al. | |
| 2012/0022490 A1 | 1/2012 | Marche et al. | |
| 2012/0152435 A1 * | 6/2012 | Schoenbeck | A61F 13/56 |
| | | | 156/66 |
| 2013/0060223 A1 * | 3/2013 | Lawson | A61F 13/62 |
| | | | 604/391 |
| 2013/0230700 A1 | 9/2013 | Schoenbeck | |
| 2014/0358107 A1 * | 12/2014 | Bader | A61F 13/49015 |
| | | | 604/385.16 |

FOREIGN PATENT DOCUMENTS

| | | | |
|---|---|---|---|
| EP | 2301502 A1 | 3/2011 | |
| EP | 2340796 A1 | 7/2011 | |
| EP | 2807999 | 12/2014 | |
| WO | WO99/13745 | 3/1999 | |
| WO | WO 2013115347 A1 * | 8/2013 | A61F 13/625 |

* cited by examiner

ABSORBENT ARTICLE WITH COMPOUND MATERIAL WEB

FIELD OF THE INVENTION

The disclosure generally relates to absorbent articles comprising at least one compound material web that includes a mechanical fastener.

BACKGROUND OF THE INVENTION

In one aspect, the invention relates to an absorbent article closure element article that includes at least one compound material web. The compound material web may comprise elastic and inelastic regions which may be separated or stamped out to form closure elements. The compound material web may comprise a nonwoven web forming a first outer side of the compound material web, elastically stretchable strips spaced apart from one another, which are disposed on the nonwoven web, a nonwoven material which covers the elastically stretchable strips on a second outer side of the compound material web, and at least one non-elastic strip of hook material which bridges a region between two adjacent elastically stretchable strips.

EP 2301502 A1 discloses the manufacture of compound material webs useful as closure elements, by laminating elastic strips in between two flat nonwoven webs. This publication discloses that a reinforcement strip is inserted between two adjacent elastically stretchable film strips. A strip of fastening material is joined to the reinforcement strip, which prevents the nonwoven material from uncontrollably tearing when the compound material web is under tension. The reinforcement strip also overlaps with the elastically stretchable film strip.

A compound material web with elastic and non-elastic areas is also disclosed in EP1736306A1. Elastic and non-elastic areas are formed in this publication by applying a continuous layer of adhesive. The continuous layer of adhesive reinforces the material to a sufficient degree whereas a discontinuous application of adhesive on the elastically stretchable film strips allows the web to elongate in its cross-direction. But it is believed that subsequent attachment of a fastening material on the outer side of the web can be problematic because the material below the hook strip is reinforced only by a continuous adhesive layer.

EP2340796A1 discloses a compound material web having a fastening material that is glued externally onto one of two flat nonwoven webs. In order to give the material sufficient strength an additional non-elastic strip of material is provided as reinforcement on the opposite side. It is believed however that the application of two opposing non-elastic material strips may be overly expensive from a material as well as process point of view.

EP768075B1 discloses an absorbent article with lateral closure elements which do not have any elastic areas. The necessary overall elasticity of the disposable nappy is achieved by arranging an elastic element in the waist region. The closure elements in this publication are in the form of lateral wings that are "rigid" and presumably are not elastically elongatable. The closure elements include a fastening material which is at least partially covered by a protective layer of nonwoven. The nonwoven here extends over the hooks of the fastening material with the result that fastening of the protective layer may be insufficient.

WO99/13745 discloses a hook material having hook-free edges, where the hook-free edges are covered by a cover material. The arrangement described is provided to be disposed in the waist region of an absorbent article in order to be able to fasten the closure elements comprising a loop material thereon.

It is therefore an object of the invention to provide an absorbent article having a compound material web with elastic and inelastic regions. It is a further objection of the invention to provide a compound material web from which absorbent article closure elements can be separated or stamped out, which enables a particularly reliable fastening of a hook material.

SUMMARY OF THE INVENTION

One aspect of the invention is directed to a closure element comprising a composite web comprising: a nonwoven web; an elastically extensible film strip joined to the top surface of the nonwoven web; a nonwoven material disposed on top of the film strip; and a strip of a fastening material disposed on top of the nonwoven web, wherein the nonwoven material overlaps the edges of the strip of fastening material and the strip of fastening material at its edges overlapped by the nonwoven material has projections which extend into the nonwoven material.

Another aspect of the invention is directed to an absorbent article, which comprises a liquid pervious layer, a liquid pervious layer and a core disposed between the liquid pervious layer and the liquid impervious layer. The absorbent article also includes at least one closure element.

DETAILED DESCRIPTION OF THE INVENTION

According to a first embodiment of the invention a compound material web comprises at least one strip of fastening material suitable for engaging a complementary fibrous web. The strip of fastening material comprises first and second longitudinal edges. The compound web also comprises at least one elastic web, which can be formed by an elastically stretchable film strip. It can be advantageous for the elastic web to overlap with the strip of fastening material. In one embodiment, the compound material web comprises at least one nonwoven material covering the film strips on a second side of the compound material web. It may include spaced-apart nonwoven strips, such that the strip of fastening material is disposed transversely. The nonwoven material may overlap edges of the strip of fastening material where the strip of fastening material at its edges overlapped by the nonwoven material has hook projections which extend into the nonwoven material. Without intending to be bound by theory, it is believed that having the hook projections integrated into the compound material web results in an improved feature through overlap by the nonwoven material. The edges of the hook material are concealed so that they are not accessible and are well protected.

The elements of the compound material web are usually glued together and/or welded together. Since at the overlapped edges of the strip of hook material the projections extend into the nonwoven material, a mechanical connection is also additionally achieved. As a result of the projections engaging in the nonwoven material, a mechanical connection in the manner of a form fit is obtained in the plane of the compound material web. Even under very high loads, a tearing of the compound material web at the transition from the elastic region to the inelastic region can thus be reliably prevented.

The present invention is based on the finding that in the compound material web known from the prior art having elastic and inelastic regions, from which absorbent article closure elements can be stamped out, an additional reinforcement in the region of the hook material is always required. According to the present invention, however, this function is taken on by the hook material itself which forms an integral component in the layer structure of the compound material web. According to an embodiment of the invention, it is provided that the projections extend through the nonwoven material. The entire thickness of the nonwoven material is then used for a mechanical anchoring in the manner of a tight fit. Starting from this, the projections extending through the nonwoven material can have heads having an angled section and/or thickened section at the ends thereof. In addition to a tight fit in the plane of the compound material web, a secure fixing of the nonwoven material is achieved perpendicular to this. In other words, the angling and/or thickening of the projections can then have the result that the nonwoven material cannot be raised upwards at the overlapping edges. In addition to an adhesive bonding usually provided, a particularly firm and secure connection is thereby achieved.

The hook material usually has a support section and free hooks between the edges covered by the nonwoven material which are provided for joining to a suitable loop material. The projections may be disposed on the support section. For example, the said hook material can be formed from a thermoplastic material where the free hooks and the projections are then pulled from or pressed out from the support section in the molten liquid state. Regardless of the precise type of manufacture, the nonwoven material at the overlapped edges may rest on the support section. In other words, the nonwoven material provided on the second outer side of the compound material web is placed directly on the support section. This has the result that the projections extend far into the nonwoven material, where the nonwoven material can also be adhesively bonded to the support section in the overlapped region.

In addition, there is the advantage that the nonwoven material at the overlapped edges is as flat as possible and well protected. In particular, within the framework of the invention the free hooks between the edges covered by the nonwoven material and the projections disposed in the covered regions can have a congruent form. The projections and the hooks then differ substantially only in that the projections are surrounded by the nonwoven material whereas the hooks are free. In principle, the projections can also be provided to a certain extent for hooking with a loop material. Within the scope of the described embodiment, the heads of the free hooks and the projections can be produced in the form of an angled section and/or thickened section before or after the joining of the individual layers of the compound material web. If the projections are already provided with heads before connecting to the nonwoven material to produce a tight fit, the nonwoven web may be guided over these heads, for which elastically resilient pressing rollers or the like can be used.

According to one embodiment of the invention, it is however provided that heads in the form of an angled section and/or thickened section are only formed after joining together the individual components of the compound material web. A non-elastic strip is then provided which initially only has stems which stretch away from the support section. If the nonwoven material is then laid, this can then be gently pierced by the stems at the edges of the non-elastic strip. Only then within the framework of the described variant are heads having an angled section and/or thickened section formed at the ends of the stems with the result that on the one hand the free hooks between the overlapped edges and the projections connected positively to the nonwoven material are obtained from the stems.

The heads are produced in particular through the action of pressure and temperature. It can also be expedient here if due to a suitable configuration of the tool provided for the forming, the stems are deformed more strongly to form the positively connected projections. A particularly intimate and reliable connection can thus be achieved between the non-elastic strip of hook material and the nonwoven material disposed in an overlapping manner at the edges. The overlap region between the strip of hook material and the nonwoven material should be selected so that a reliable fastening is possible. The overlap region can, for example, lie between about 2 mm and about 30 mm, between about 8 mm and about 20 mm.

The elastically stretchable strips may be formed by an elastically stretchable film. The nonwoven material covering the elastically stretchable strips or film strips on the second side of the compound material web is expediently in the form of spaced-apart nonwoven strips. Within the framework of the invention, the elastically stretchable strips can either be guided directly onto the non-elastic strip of hook material or end at a distance of typically a few millimeters from the non-elastic strip of hook material. According to the invention the transition region on the second outer side is covered and protected by the nonwoven material provided there. The nonwoven material therefore extends in the direction of the non-elastic strip of hook material beyond the elastically stretchable strips.

According to one embodiment of the invention, the hook material is fastened directly to the flat nonwoven web. The elastically stretchable film strip can also be fastened directly to the nonwoven web.

In principle, various possibilities come into consideration for the fastening. The fastening can, for example, be accomplished by adhesive which can be applied if desired over the complete area or only in some areas. Depending on the type of adhesive bonding and depending on the materials and stresses, a strip-shaped adhesive bonding can be sufficient to securely fasten the hook material. Here it should also be borne in mind that an increased strength is achieved due to the positive joining of the hook material to the nonwoven material on the second outer side.

In principle, adhesive can be saved by a strip-shaped adhesive binding, resulting in a reduction in costs. It should also be borne in mind that suitable adhesives are not only relatively expensive but can also adversely affect the elasticity. This negative influence of the adhesive is reduced by a strip-shaped application underneath the elastically stretchable strip. A strip-shaped application of adhesive parallel to the extension of the elastically stretchable strip is particularly advantageous where the individual absorbent article closure elements formed from the compound material web are stretched transversely thereto during use.

The elastically stretchable strips may consist of a film of a suitable thermoplastic elastomer, where a polymer from the group of styrene-butadienestyrene block copolymers (SBS), styrene-isoprene-styrene block copolymers (SIS), styrene ethene-butene-styrene block copolymers (SEBS), elastic polyethylene copolymers, elastic polypropylene copolymers, elastic polyurethane copolymers, elastic polyamide copolymers or a mixture of these polymers is suitable. In addition to using monofilms, co-extruded films can also be used where co-extruded film having a plurality of identical layers are suitable. Film strips having a thickness between about 10 and about 130 µm are suitable.

The nonwoven material covering the elastic strips on the second outer side and the nonwoven web disposed on the opposite side of the compound material web are usually not elastic themselves but are stretchable to a sufficient extent in order to be able to form the elastic regions of the compound material web. The necessary stretchability can however also be achieved by activating the compound material web by a first stretching in which the nonwoven layers are partly destroyed, i.e. torn. The nonwoven gives the compound material web a soft, textile feel.

The subject matter of the invention is also a method for manufacturing a compound material web, wherein a nonwoven web, elastically stretchable strips, strips of a nonwoven material and a non-elastic strip having projections at its edges are provided. The non-elastic strip is applied indirectly or directly to the nonwoven web, where the strips of the nonwoven material are disposed on the edges of the non-elastic strip in an overlapping manner such that the projections extend into the nonwoven material. As described previously, the projections can comprise stems and have heads with an angled section and/or thickened section at their ends.

The strips of nonwoven material can be supplied either before or after the non-elastic strip.

Thus, according to a first variant of the invention, the nonwoven web, the elastically stretchable strips and the strips of nonwoven material can be joined together, where a spacing remains between the elastic strips and where the strips of nonwoven material there extend with their free ends over the elastically stretchable strips. These free ends are then unfolded in order to be able to arrange the non-elastic strip of hook material, or the non-elastic strip from which the hook material is formed, between the elastically stretchable strip. The unfolded sections of the nonwoven material are then placed back onto the hook material, with the result that a positive connection with the projections is obtained in the overlapping region. If the projections extend through the nonwoven material, the projections can then be formed in the manner described by action of pressure and/or temperature to obtain a tight fit in the vertical direction. At the same time, free hooks can also be formed between the strip of hook material in the manner described.

If firstly the hook material and then the strips of nonwoven material are supplied, the strips of the nonwoven material can be placed directly overlapping onto the hook material and the elastically stretchable strips, where a subsequent folding is then no longer necessary.

A further aspect of the present invention which has independent inventive importance, relates to the formation of a hook material. This hook material is particularly suitable for the previously described compound material web, but can fundamentally also be used in other areas.

In order to form the hook material a polymer melt is fed from a wide-slit nozzle into a gap between a roller and a belt guided in sections along the surface of the roller, where the roller and/or the belt have a structuring provided for forming hooks. Depending on the configuration of the method, either complete hooks with stems and end-side heads or initially only the stems of the hooks or the projections can be formed, with the heads then being produced subsequently. Hooks are understood within the framework of the invention as elements which are suitable for hooking into an associated material, for example, a textile knitted with free loops or a nonwoven having loops. The hooks can have ends bent at the stems or mushroom-shaped broadenings as heads.

Since an initially still-liquid polymer melt can be supplied from the slotted nozzle onto the gap, the formation of the hooks of the hook material can be varied very freely. Thus, for example, the structuring provided to form the hooks can be interrupted at sections of the belt or roller in order to form no hooks there. In particular, the structuring can be interrupted in the transverse direction and/or circumferential direction where hook-free regions are produced by a flat surface. In addition to producing regions with hooks or projections and hook-free regions, in the method described the roller gap and therefore the local thickness of the hook material produced can be adjusted by an appropriate contouring of the belt and/or roller.

If, according to a first variant to form the hook material, a smooth belt, also designated as sleeve, and a structured roller (chill roll) are used, the stems of the hooks or projections are produced by the structured, usually cooled roller (chill roll).

Within the framework of the structuring, recesses or cavities are formed in the roller to form the stem of the hook or projections. To this end, for example, the roller surface can be processed by an etching method or by using a laser. The number and distribution of the cavities can be variably adapted to the respective application of the hook tape to be formed.

The belt can be produced, for example, completely seamlessly by a galvanic process. Such a belt, which is also designated as smooth belt depending on the application, is usually tensioned between two tempered rollers of which at least one can be driven. The tensioned belt is usually pressed by a movable roller against the structured cooled roller. By pressing the belt in a usually variably adjustable wrap-around angle, it is achieved that the initially still-liquid polymer melt fills the recesses or cavities of the structured roller. An additional ventilation can usually be dispensed with here, where a multilayer configuration of the roller for ventilation is not required. Through the contact with the circulating belt during the formation of the stems of the hooks or projections the cooling can be better controlled, so that manufacture is also possible at a very high production rate. By using the described belt, a particularly uniform, smooth and high-quality back of the hook material can be produced.

As already explained previously, the structuring can be interrupted in the longitudinal direction, transverse direction or in any direction to produce hook-free regions.

According to a second variant to form the hook material, a smooth roller and a structured or perforated belt are used. With a perforated belt, a sufficient ventilation of the individual holes to produce the stems of the hooks or projections is ensured under all circumstances. The length of the stems to be formed can also be adjusted by the thickness of the belt. Alternatively the length of the stems can also be adjusted by the pressing pressure of the belt on the roller where the holes of the perforation are only partially filled at a reduced pressing pressure. The height of the stems of the hooks can be varied by varying the pressing pressure without exchanging the belt.

Depending on the requirement and area of use, the hook material can be constructed of different materials both as single-layer and as multilayer. With a single layer structure polyolefin materials such as polyethylene (PE), polypropylene (PP), mixtures of the said polymers and a copolymer of polyethylene and polypropylene are particularly suitable. In one embodiment, stiff PP types are used which can be present both as homo- and as copolymers. Furthermore however, other polymers are also suitable for a single-layer or multilayer structure. Particularly advantageous are comparatively stiff materials such as cyclo-olefin copolymer (COC), polyesters such as polyethylene terephthalate (PET), polyamides (PA) such as PA 6 and PA 6.6 or also polymethylmethacrylate (PMMA).

Through a multilayer structure of the hook tape, the partly conflicting requirements of, for example, stiffness, flowability during manufacture and compatibility to the adjacent layers in the laminate can advantageously be fulfilled. According to a first variant, largely pure-type structures or at least structures completely of polyolefin are possible whereby in particular recycling is made easier. For example, in a three-layer structure polypropylene (PP) can be provided for all the layers, where however the layer from which the hooks or projections are to be formed is specially selected with regard to improved embossing behavior with a high flow index (MFI) whereas the other layers are specifically optimized with regard to the required stiffness of the hook tape.

In addition to such a pure-type structure, a multilayer structure of various types of materials is possible, where optionally polyolefin-based materials, in particular PP are used in the outer layers. With a structure comprising at least three layers, an interior core layer can be selected with regard to a maximum stiffness. Whereas in a five-layer structure an adhesion promoter layer is provided between the core layer and the outer layers, in a three-layer structure a sufficient joining of the layers to one another by functionalized or modified polyolefins can be achieved.

The thickness of the hook material below the hooks or projections is typically between about 20 and about 180 µm, between about 70 and about 140 µm.

The present invention will now be explained with reference to the drawings which merely show examples of embodiments.

Figure 1:
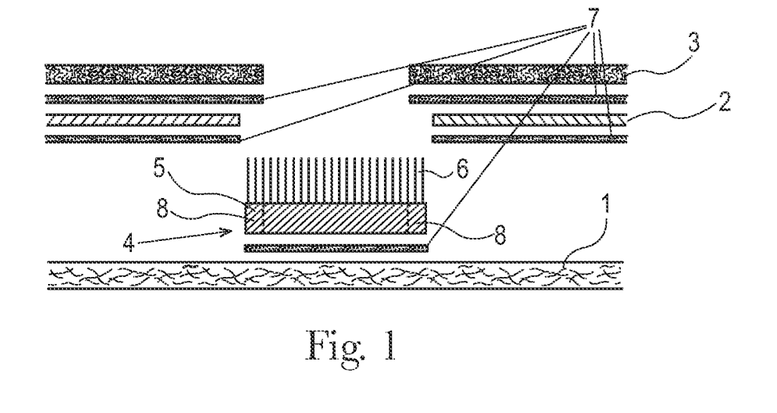
FIG. 1 is a schematic exploded cross-section of a compound material web.

FIG. 1 shows in a cross-section the individual components from which a compound material web having elastic and inelastic regions is formed, from which absorbent article closure elements can be stamped out or separated. The compound material web comprises a flat nonwoven web 1 which forms a first outer side of the compound material web. In order to produce the elastic regions of the compound material web, elastically stretchable film strips 2, which are spaced apart parallel to one another, are disposed on the nonwoven web 1, where these film strips 2 are covered by a nonwoven material 3. The nonwoven material 3 disposed in the form of nonwoven strips covers the film strips 2 completely and forms a second outer side of the compound material web in some regions. In addition, a non-elastic strip 4 is provided from which a hook material is formed. The non-elastic strip 4 has a support layer 5 and upwardly projecting stems 6.

The components described can be joined to one another in various ways. In particular, an extensive or sectional adhesive bonding by means of adhesive 7 or an ultrasound welding can be accomplished. In the case of adhesive bonding provided only in sections, the joining is easily accomplished by adhesive strips which extend along the longitudinal direction of the strip-shaped elements described.

FIG. 1 shows the individual components of the compound material web where an extensive application of adhesive 7 is shown merely as an example. It can be seen in FIG. 1 that the two elastically stretchable film strips 2 are disposed laterally to the non-elastic strip 4 whilst the nonwoven material 3 overlaps edges 8 of the non-elastic strip 4. If the non-elastic strip 4 is initially applied to the nonwoven web 1 before the elastically stretchable film strips 2 and the strips of nonwoven material 3 are supplied, at the overlapping edges 8 the nonwoven material 3 is pierced directly by the stems 6 at the edges 8 whilst being supplied with the result that the nonwoven material 3 is held by the stems 6 (FIG. 2).

The stems 6 then form projections 9 at the edges 8 which extend into the nonwoven material 3 and through the nonwoven material 3. In order to form free hooks 10 between the overlapped edges 8, the stems 6 are formed by means of a suitable tool 11 under the action of pressure and temperature, where heads having an angled section and/or thickened section are produced. The stems 6 at the overlapped edges 8 are formed in the same way, where the nonwoven material 3 is not only fixed in a tight fit in the plane of the compound material web but also perpendicular thereto. Within the framework of the invention a tool 11 can be used which deforms the stems 6 forming the projections 9 more severely that the stems 6 from which the free hooks 10 are formed.

Figure 4:
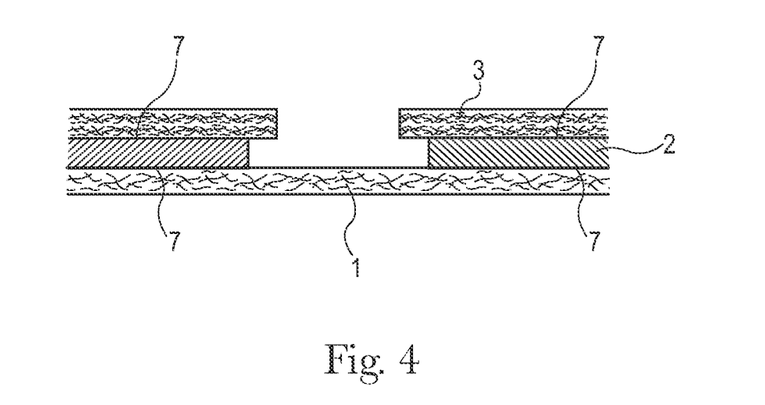
FIGS. 4-6 are alternatives of the method for manufacturing the compound web material.
Figure 5:
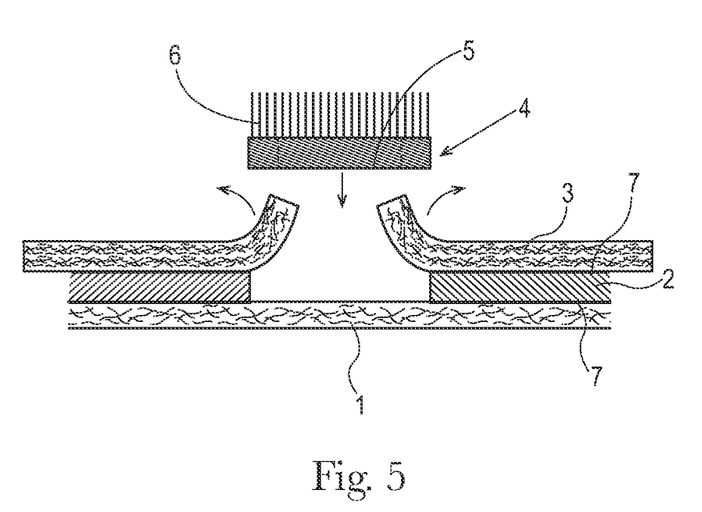
Figure 6:
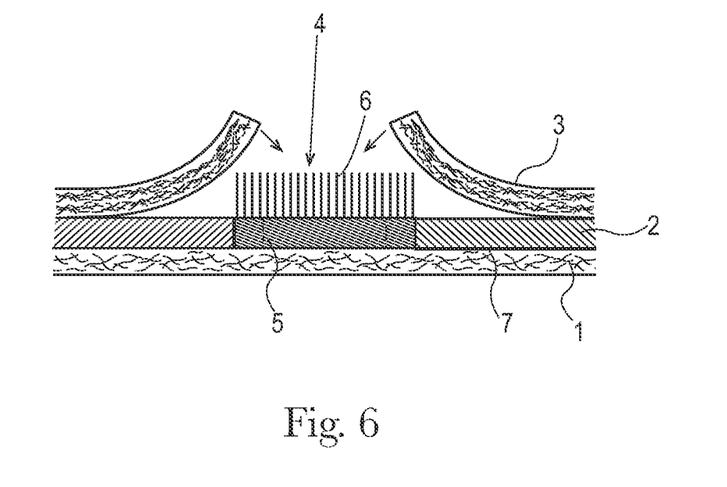

FIGS. 4 to 6 show an alternative procedure for the manufacture of the compound material web where the nonwoven web 1, the elastic film strips 2 and the strips of nonwoven material 3 are joined together, for example, by adhesive 7. As also shown in FIG. 1, the strips of nonwoven material 3 extend beyond the film strips 2. The non-elastic strip 4 is then arranged by folding back the free lateral ends of the nonwoven material 3 (FIG. 5).

Figure 2:
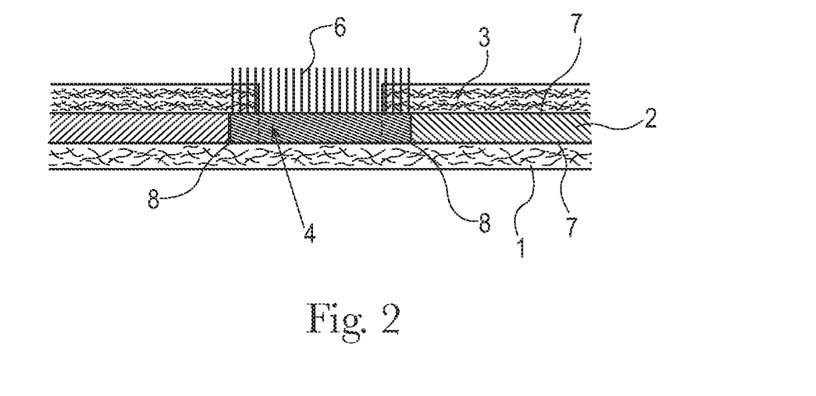
FIG. 2 is a schematic cross-section of a compound material web.
Figure 3:
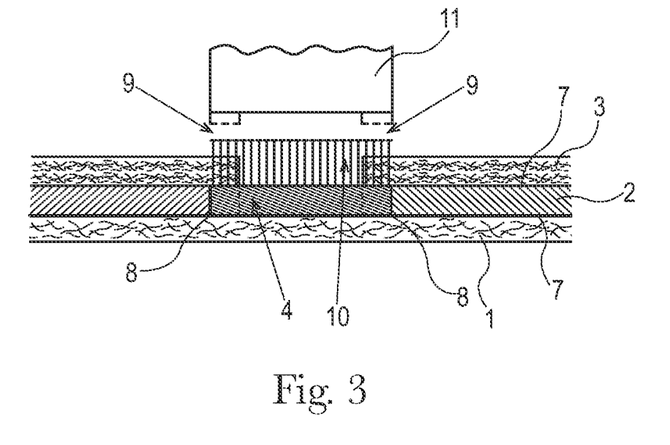
FIG. 3 is a process step for producing hooks.

After folding back the nonwoven material (FIG. 6), the arrangement according to FIG. 2 is also achieved in this alternative process, where a forming of the stems 6 then takes place subsequently.

Figure 7:
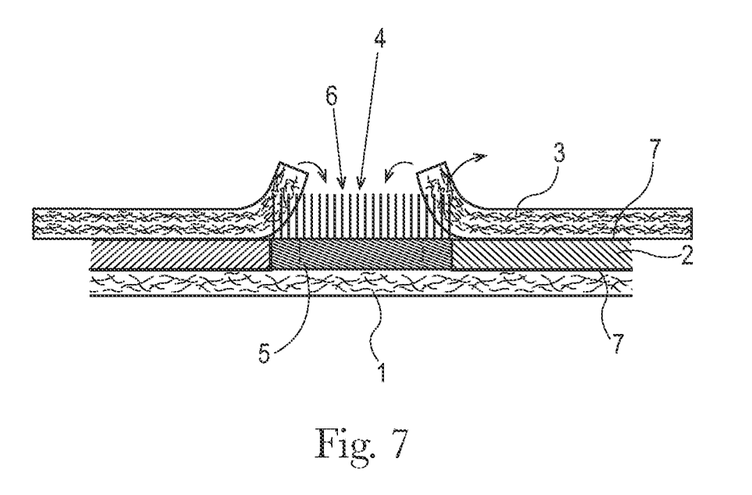
FIG. 7 is an alternative schematic cross-sectional representation of a compound material web.

FIG. 7 shows another alternative embodiment of the invention, where the stems 6 at the overlapped edges 8 have a shorter length. The projections 9 formed by the stems 6 at the overlapping edges 8 then only extend into the nonwoven material 3 but not through the entire nonwoven material 3. Nevertheless a reliable fixing is achieved at least in the plane of the compound material web, where the nonwoven material 3 can be adhesively bonded to the support section 5 of the non-elastic strip 4.

Figure 8:
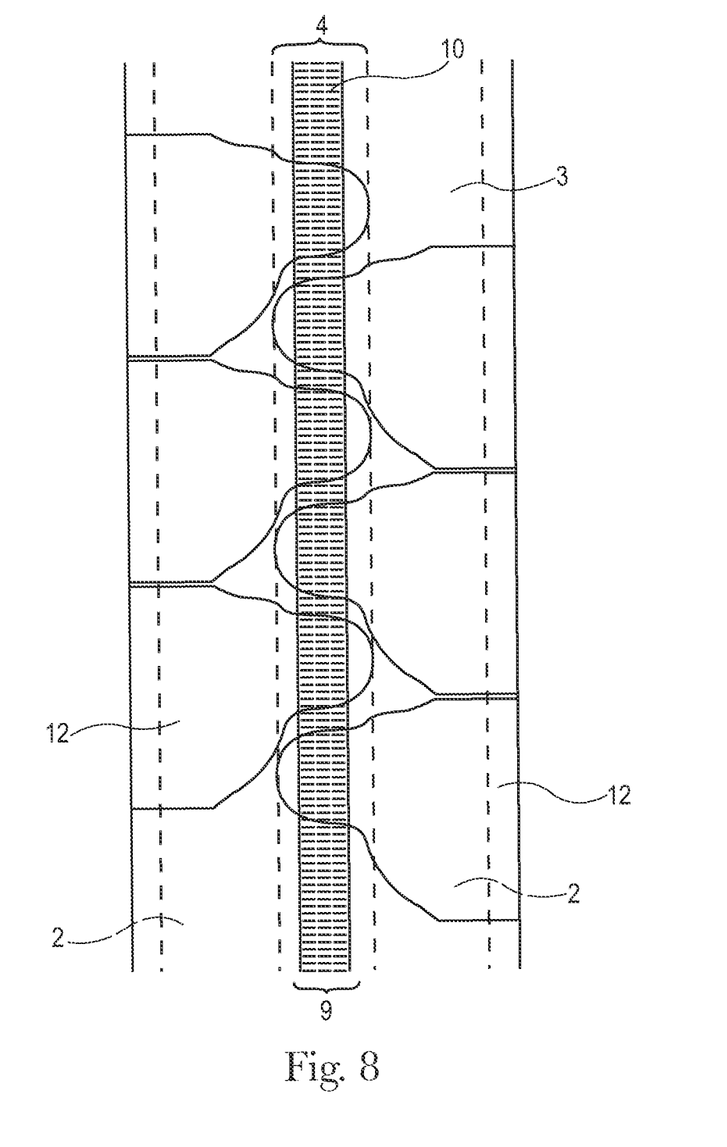
FIG. 8 is a schematic top view of a compound material web and closure members cut from the compound material web.

FIG. 8 shows a possible cutting or stamping pattern to produce individual closure elements 12. In the embodiment according to FIG. 8 each closure element 12 comprises the region of the non-elastic strip 4 provided with hooks 10 over its entire width. In addition, a free end of the closure element 12 is formed by a section of the compound material web which comprises the projections 9 next to the hooks 10. In particular, if the projections 9 extend through the nonwoven material 3, a strong deformation can be provided with the tool 11 during manufacture in order to produce a smooth gripping section for a user, which is as uniform as possible.

Figure 9:
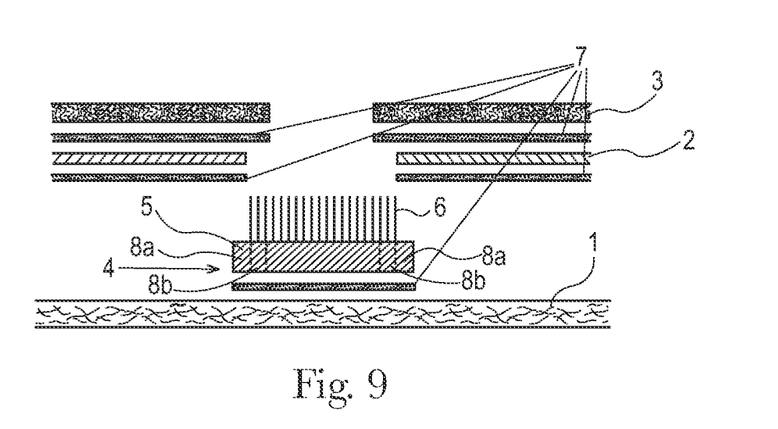
FIG. 9 is an alternative schematic exploded cross-section of a compound material web.

Following FIG. 1, FIG. 9 shows another alternative embodiment of the compound material web with a first outer edge section 8a covered by the nonwoven material 3 being free of hooks 10 or stems 6. While the elastic film strips 2 end at the outer edge section 8a, the nonwoven material 3 extends further until a second, more inwardly lying edge section 8b comprising upwardly projecting stems 6.

Figure 10:
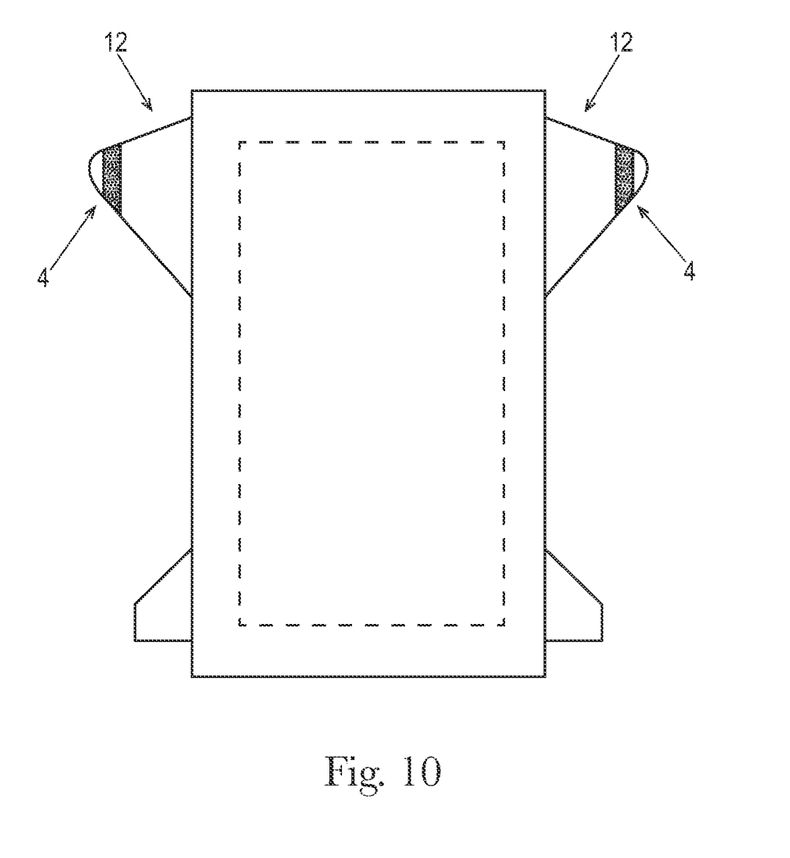
FIG. 10 is a schematic top view of an absorbent article that includes a pair of closure elements.

As previously discussed, closur elements made from any of the previously discussed compound material webs are suitable for use with absorbent articles such as for example infant or adult diapers. In an embodiment shown in FIG. 10, at least one but preferably a pair of closure elements 12 are attached to the chassis of an absorbent article. The chassis may include a liquid pervious layer (also known as a topsheet), a liquid impervious layer (also known as a backsheet) and a core disposed between the liquid pervious layer and the liquid impervious layer. The core is adapted to absorb and retain liquids, such as for example urine. In one embodiment, a pair of closur elements is disposed in an end section of the chassis, which in the case of an infant diaper can be the back waist section of the chassis. A non-limiting example of an absorbent article that includes a pair of closure elements is represented in FIG. 10.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A closure element comprising
    a composite web comprising:
    a nonwoven web;
    an elastically extensible film strip joined to the top surface of the nonwoven web;
    a nonwoven material disposed on top of the film strip; and
    a strip of a fastening material disposed on top of the nonwoven web,
    wherein the nonwoven material overlaps the edges of the strip of fastening material and the strip of fastening material at its edges overlapped by the nonwoven material has projections which extend into and through the nonwoven material.

2. The closure element of claim 1 wherein the composite web material has at least one elastic region and at least one inelastic region.

3. The closure element of claim 1 wherein the ends of the projections have heads having an angled section or a thickened section.

4. The closure element of claim 1 wherein the projections are disposed on a support section of the strip of fastening material, wherein the nonwoven material rests on the support section at the overlapped edges.

5. An absorbent article comprising:
    a liquid pervious layer;
    a liquid impervious layer;
    a core disposed between the liquid pervious and the liquid impervious layers; and
    a composite web comprising:
    a nonwoven web;
    an elastically extensible film strip joined to the top surface of the nonwoven web;
    a nonwoven material disposed on top of the film strip; and
    a strip of a fastening material disposed on top of the nonwoven web,
    wherein the nonwoven material overlaps the edges of the strip of fastening material and the strip of fastening material at its edges overlapped by the nonwoven material has projections which extend into and through the nonwoven material.

6. The absorbent article of claim 5 wherein the composite web material has at least one elastic region and at least one inelastic region.

7. The absorbent article of claim 5 wherein the ends of the projections have heads having an angled section or a thickened section.

8. The absorbent article of claim 5 wherein the projections are disposed on a support section of the strip of fastening material, wherein the nonwoven material rests on the support section at the overlapped edges.

* * * * *